United States Patent [19]

Nuno Bardosa Nolasco et al.

[11] Patent Number: 5,714,312
[45] Date of Patent: Feb. 3, 1998

[54] PROCEDURE FOR THE DETECTION AND IDENTIFICATION OF VIRAL AND SUBVIRAL PATHOGENS

[75] Inventors: Gustavo Nuno Bardosa Nolasco, Faro, Portugal; Carmen De Blas Beorlegui, Madrid, Spain; Maria José Borja Tome, Madrid, Spain; Fernando Pons Ascaso, Madrid, Spain; Vincente Torres Pascual, Madrid, Spain

[73] Assignee: Instituto Nacional de Investigacion y Techologia Agraria y Alimentaria, Spain

[21] Appl. No.: 389,067

[22] Filed: Feb. 14, 1995

Related U.S. Application Data

[63] Continuation of Ser. No. 70,729, Jun. 2, 1993, abandoned.

[30] Foreign Application Priority Data

Jun. 12, 1992 [ES] Spain ............................... 9201232

[51] Int. Cl.$^6$ ............... C12Q 1/70; C12Q 1/68; C12P 19/34
[52] U.S. Cl. ..................... 435/5; 435/6; 435/91.2
[58] Field of Search ................ 435/6, 91.2, 5; 935/77, 78

[56] References Cited

FOREIGN PATENT DOCUMENTS

| 0145356 | 6/1985 | European Pat. Off. . |
| 0201184 | 12/1986 | European Pat. Off. . |
| 0366448 | 5/1990 | European Pat. Off. . |
| 0469348 | 2/1992 | European Pat. Off. . |
| 2537725 | 6/1984 | France . |
| 9117442 | 11/1991 | WIPO . |

OTHER PUBLICATIONS

J. of Virol Meth. vol. 33, 1991, Wetzel et al.: "A Polymerase Chain Reaction Assay Adapted to Plum Pox Polyvirus Detection", pp. 355–365.

Ann. Appl. Biol., vol. 117, 1990, Vunsh, R. et al.: "The Use of Polymerase Chain Reaction (PCR) For The Detection Of Bean Yellow Mosaic Virus In Gladiolus", pp. 561–569.

Proc. Natl. Acad. Sci. USA, vol 90, pp. 10168–10172, Nov. 1993, Agricultural Sciences, Passmore, et al., "Beet western yellows virus–associated RNA . . . ".

Current Communications in Molecilar Biology, Cold Spring Harbor Laboratory, 1983, "Plant Infectious Agents: Viruses, Viroids, Virusoids, and Satellites."

Aramburu et al., J. Virol–Methods 33:1–11 (1991) "Detection of ds-RNA by elisa . . . ".

Viscidi et al., J. Clin. Microbiol 27:120–125 (1989) "Monoclonal Antibody Solution Hybridization Assay . . . ".

Boye et al., N. A. Res 18:4926 (1990) "Nucleotide sequence of cDNA encoding . . . ".

Daniel et al., Virology 174:87–94 (1990) "Protection from Lethal Corona virus infection . . . ".

DNAS 87:2867–2871 (1990).

Primary Examiner—Eggerton A. Campbell
Attorney, Agent, or Firm—Ostrolenk, Faber, Gerb & Soffen, LLP

[57] ABSTRACT

A method for detecting and quantifying viral or subviral pathogens in the test sample in which antibodies against a component of the viral or subviral pathogen is immobilized on a substrate. The test sample is placed in contact with the immobilized antibody and then a DNA primer complementary to a fragment or the total genome of the viral or subviral pathogen is permitted to hybridize to the RNA or DNA of the immobilized viral or subviral pathogen. The DNA is then amplified and the amplification products are detected and quantified.

36 Claims, 2 Drawing Sheets

FIG.1

PROCEDURE FOR THE DETECTION AND IDENTIFICATION OF VIRAL AND SUBVIRAL PATHOGENS

This is a Continuation of application Ser. No. 08/070,729 filed on Jun. 2, 1993 now abandoned.

OBJECT OF THE INVENTION

The present invention refers to a new procedure for the detection and identification of viral and subviral pathogens, which combines the immobilization of the pathogen by means of antibodies attached to the surface of the wells of a microtitration plate, with the enzymatic amplification of fragments of the viral genome and the spectrophotometric quantification of the same or their identification by electrophoretic techniques, a viral pathogen being taken to be any virus that replicates inside protoplasts, prokaryotic or eukaryotic cells, whether differentiated or not, and at the expense of some enzyme of such protoplasts or cells, while a subviral pathogen is defined as any viroid, virusoid, satellite virus, viral satellite RNA, which replicates inside plant cells, whether differentiated or not, or their protoplasts and at the expense of any enzyme of such protoplasts or cells, while the term biological sample is given to prokaryotic cells, protoplasts, differentiated or undifferentiated eukaryotic cells, mycelia, plant or animal tissues, plant or animal organs, "in vitro" cultivation media of any of the preceding entities, plant or animal systems and plant or animal organisms, the same term being used to describe any product of secretion, excretion or transformation of any of the preceding entities.

BACKGROUND TO THE INVENTION

In living cellular beings the detection and identification of viral and subviral pathogens are common practices in health control, epidemiological studies and in search programs for genes that confer resistance on such pathogens. In the three cases it is necessary to process a large number of samples, without ambiguity and at low cost, for short periods of time. It is therefore desirable that the methods employed should combine the following characteristics: sensitivity, precision and reproducibility, speed of implementation, simple and economic installations, equipment and materials, and also that they should not require personnel with advanced technical training (Matthews, R. E. F. (1991), Methods for Assay, Detection and Diagnosis in Plant Virology. 3rd edition, 11 pp. Academic Press Inc. New York).

The methods of detection and identification of viral and subviral pathogens may be based on the analysis of their interaction with the host, the physical properties of their particles or on the properties of their proteins and/or nucleic acids.

The analysis of host-pathogen interaction is usually slow, requires heavy investment in installations, and the results obtained very much depend on the medium and are sometimes completely subjective.

The study of the physical properties of RNA particles and molecules in viral and subviral pathogens employs slow and complex techniques such as analytical ultracentrifugation or electron microscopy, which require expensive and sophisticated instrumentation and highly qualified personnel.

Obviously, as a result of the said limitations, none of these techniques is suitable for routine use in the detection and identification of viral and subviral pathogens.

Among the methods of detection and identification of viral and subviral pathogens based on the study of the properties of their proteins, the immunological technique known as ELISA is commonly used (Clark, M. F. & Adams, A. N. (1977), J. Gen. Virol. 34: 475–483). In most cases the technique meets the conditions required of a routine detection method. However, it has the following limitations:

- It is not easily applicable in the detection of subviral pathogens as in the majority of cases its genomes do not codify for any structural protein.
- It gives rise to problems of sensitivity in the detection of some viruses with a low infection rate. Examples of these are the plant viruses limited to phloems (geminivirus, luteovirus or closterovirus) or some retroviruses such as HIV (AIDS) or others closely restricted to an organ or tissue (HEPATITIS, NERVOUS TISSUE VIRUS, etc.).
- When using polyclonal antibodies the results may lack reproducibility owing to the variability between different lots of antibody.
- The limited sensitivity also hinders early detection of the infection.

Advances in the knowledge of the structure and function of the nucleic acids of viral and subviral pathogens have provided a wide range of techniques applicable to the characterization of these pathogens. In theory, at least, the most suitable of these for detecting and identifying viral and subviral pathogens are molecular hybridizations (Müller, R. et al. (1991), J. of Virol. Meth. 34: 141–148; Robinson, D. I. & Romero, J. (1991), J. of Virol. Meth. 34: 209–219; Kanematsu, S. et al. (1991), J. of Virol. Meth. 35: 189–197) and the polymerase chain reaction (PCR) (Erlich, H. A. et al., EP 258.017; Cohen, S. N. U.S. Pat. No. 4,293,652; Mullis, K. B., EP 201184; Mullis et al., EP 200362; Saiki, R. K. et al., Science 239: 487–491 (1988); Mullis, K. B. et al., Meth. Enzymol. 155: 335–350 (1987); Scharf, R. K. et al., Science 233: 1076–1079 (1986).

Molecular hybridizations of nucleic acids have occasionally been used in the detection and identification of viral and subviral pathogens. However, the use of radioactively marked probes means that these techniques are costly, they require special installations and are tedious when processing a large number of samples. Non-radioactive marking with biotin or digosigenine solves some of these problems, although sensitivity is limited.

Polymerase chain reaction (PCR) is a very efficient and specific method, theoretically capable of synthesizing over a million copies of a single sequence of a DNA model. This method has been used to detect viral pathogens with a DNA genome (Rybicky, E. P. & Hughes, F. L. (1990), J. Gen. Virol. 1: 2519–2526; Pasamontes et al. (1991), J. of Virol. Meth. 35: 137–141; Soler, C. et al. (1991), J. of Virol. Meth. 35: 143–147). A method which combines the synthesis of complementary DNA (cDNA) using reverse transcriptase with viral RNA as a template and its subsequent amplification by polymerase chain reaction (RT-PCR) has been used in the detection and characterization of various viruses with RNA genoma, both animal (Lin, S. T. et al. (1991), J. of Virol. Meth. 35: 227–236; Meyer, R. F. et al. (1991), J. of Virol. Meth. 34: 161–172), and plant (Vunsh, R. et al. (1990), Ann. Appl. Biol. 117: 561–569; Korschineek et al. (1991), J. Virol. Meth. 31: 139–146; Borja, M. J. & Ponz, F. (1992), J. Virol. Meth. 36: 73–86). The sensitivity of the RT-PCR method is much greater than that of the ELISA technique (Borja, M. J. & Ponz, F. (1992), J. Virol. Meth. 36: 73–86). Nevertheless, the disadvantages of using the RT-PCR method under routine conditions are the use of phenol, a highly toxic product, in an initial stage of nucleic acid extraction, and the detection of the products of amplification by electrophoresis in gel.

Wetzel, T. et al. (1991), J. of Virol. Meth. 33: 355–365, and Borja, M. I. & Ponz, F. (1992), J. of Virol. Meth. 36: 73–86, respectively, have described the detection of the sharka virus and the walnut strain of the cherry leaf-roll virus (wCLRV) in tissue homogenates by means of RT-PCR without previous phenolization, however, these methods have not been successful generally in identifying other plant viruses. Jansen, R. W. et al. (1990), Proc. Nat. Acad. Sci. USA, 87: 2867–2871, describes the detection of the hepatitis A virus by RT-PCR, introducing a stage of purification of the virus by immobilized antibodies on the walls of an Eppendorf tube, followed by heat fracture of the virion prior to the RT and enzymatic amplification. This method is not generally applied in the detection and identification of plant viruses. Liang, T. & Wands, J. R. (1988), U.S. patent application Ser. No. 262,347, describe a method of detection of the hepatitis B virus which combines the capture of the pathogen using antibodies attached to CNBr-activated SEPHAROSE, with enzymatic amplification of the viral DNA and electrophoretic identification of the products of amplification. The method is tedious for routine application.

SUMMARY OF THE INVENTION

The procedure for the detection and identification of viral and subviral pathogens, which the invention proposes, consists of the following steps:

A). Immobilisation of the pathogen by using antibodies against coat proteins in the case of viral pathogens and satellite viruses or antibodies against double-chain RNAs in the case of other subviral pathogens. The antibodies are immobilized in the polystyrene surface of the wells of a microtitration plate.

B). Direct synthesis, on the same plate, of the complementary DNA (cDNA) with a fragment of the genome of the viral or subviral pathogens, without stages of intermediate denaturing of the virions or related structures.

C). Enzymatic amplification, on the same plate, of the cDNA or of a fragment of the genome of DNA virus.

D). Quantification on the same plate of the products of amplification by employing spectrophotometric techniques.

E). Identification of the products of amplification, if desired, by means of electrophoretic techniques.

In addition to complying with the conditions required for it to be used as a routine method for detecting and identifying viral and subviral pathogens, the procedure proposed by the invention has the following advantages, among others:

It is a general procedure, since its use has enabled the detection and identification in biological samples of very different origins, of viruses with such distinct biological and architectural characteristics as those shown by members of the groups: tobamovirus, potyvirus, closterovirus, luteovirus, nepovirus, cucumovirus and tospovirus.

It permits the identification and detection of subviral pathogens.

It is applicable to the detection and identification of viral pathogens for which no antibodies are available against the capsid proteins, since antibodies may be used against double chains of RNAs in the immobilization of the pathogen.

Its high sensitivity permits the detection and identification of viral pathogens with a low capacity of infection.

It permits early detection and identification of host infection by viral and subviral pathogens.

It does not require excessive or complex manipulation.

The operations of immobilization amplification and spectrophotometric quantification are carried out on the same microtitration plate.

FIG. 1 shows the results obtained, in terms of electrophoretic mobility, of procedures performed for identification and detection of pathogens according to Examples 1–8 described below.

FAVORED METHOD FOR CARRYING OUT THE INVENTION

Figure 2:
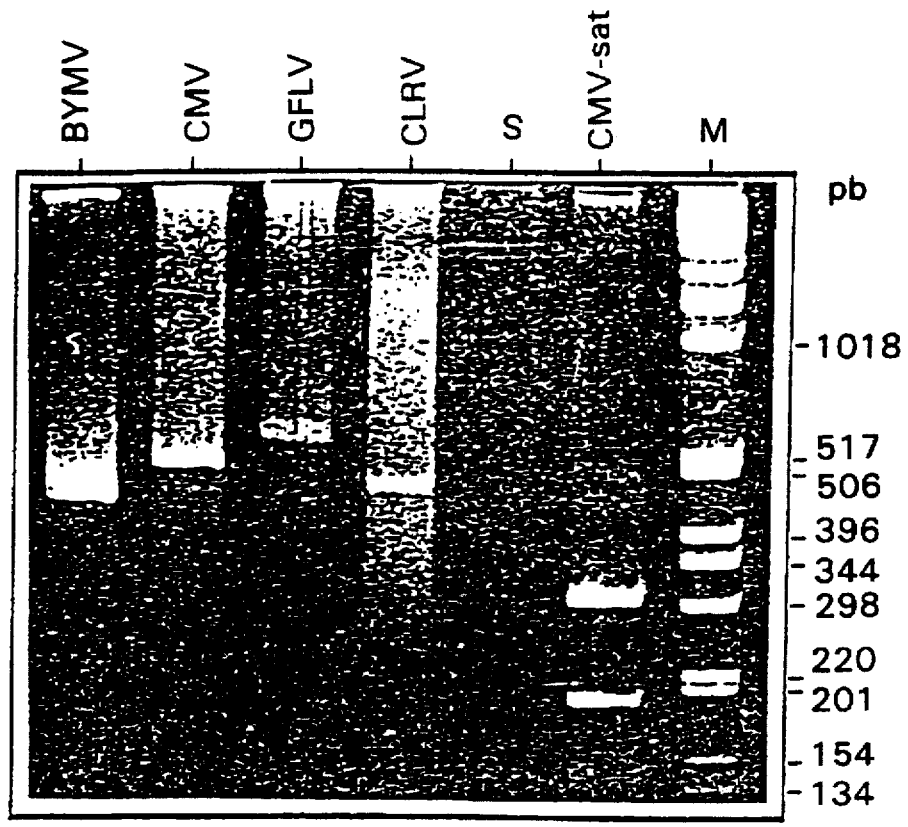
FIG. 2 shows the results obtained, in terms of electrophoretic mobility, of the procedures performed for identification and detection of pathogens according to Example 10 described below.

More specifically and in order to put into practice the proposed procedure of detection and identification of viral and subviral pathogens, the corresponding antibody is attached to the inner surface of the wells of a microtitration plate, filling them with a solution of the antibody in a basic pH buffer, and incubating the whole at temperatures not exceeding 50° C. during a period of at least 15 minutes and washing the wells several times with a saline solution containing a detergent and an almost neutral pH buffer.

Next, the samples to be analyzed are distributed in the wells and the whole is incubated at a temperature not exceeding 20° C. for at least 15 minutes, followed by several washings with the aforesaid saline solution.

In the case or viral pathogens with DNA genome, the amplification is carried out by adding to the wells the necessary reagents for the enzymatic reaction and submitting the whole to a series of cycles of denaturalization, annealing and synthesis. The temperature and duration of each cycle depend on the nucleotide sequence of the fragment to be amplified.

In the case of viral pathogens with RNA genome or subviral pathogens, prior to amplification the complementary DNA (cDNA) is synthesized with the fragment of genome to be amplified, for which purpose the necessary reagents are added to the wells for the synthesis of the cDNA and the whole is incubated at a temperature of at least 15° C., continuing with the amplification stage in the manner described.

Following amplification, a solution of bisbenzymide and the complex formed with the DNA is quantified spectrophotometrically.

The identification of the products of amplification is carried out by electrophoretic techniques.

There follows a series of examples of practical realization of the procedure for the detection and identification of viral and subviral pathogens which constitutes the object of the present invention:

EXAMPLE 1

Detection and Identification of a Potyvirus

Potyviruses are viral pathogens. Their particles are elongated, flexible, about 12 nm in diameter and between 680 and 900 nm in length. Their genoma is a linear molecule of single-stranded RNA of approximately 10 kilobases (Francki, R. I. B. et al., in Atlas of Plant Viruses, Vol. II, 284 pp. (1985), CRC Press, Boca Raton, Fla.). A representative member of the group is the bean yellow mosaic virus (BYMV). The detection and identification of this virus in broad-bean plants (Vicia faba L.) is described in this example.

Leaf samples from plants infected with BYMV are homogenized individually in the ratio 1/10 (weight/volume), with a buffer of Tris-HCl 0.5M pH 8.0, containing 2% polyvinylpyrrolidone, 1% polyethylenglycol 6000, 0.8% NaCl, 0.005% Tween 20 and 0.02% sodium acid. Aliquots of 50 microliters of the homogenates are distributed in the wells of a microtitration plate previously coated with BYMV antiserum, following the procedure described by Clark, M. F. & Bar-Joseph, M. (1984), Methods in Virology 7, 51–85.

The reverse transcription is carried out on the same plate, adding to each well 20 microliters of buffer Tris-HCl 0.05M pH 8.3, 0.075M KCl, 0.003M MgCl$_2$, 0.001M in each dNTP, 200 units of M-MLV reverse transcriptase and 1 micromole in the oligonucleotide primer of the synthesis in the direction 5'–3'. After incubating at 37° C. for 1 hour, 80 microliters of composition amplification mixture are added to each well, with final concentrations of: buffer Tris-HCl 60 mM pH 9, 0.015 mM KCl, 2.1 mM MgCl$_2$, 20 mM (NH$_4$)$_2$SO$_4$ in each dNTP, 0.005% bovine serum albumen (BSA) and 0.2 mM in each oligonucleotide primer. The oligonucleotide primers used (Table 1) were designed on the basis of existing information on the virus genome sequence. (Hammond, J. & Hammond, R. W. (1989), J. Gen. Virol. 70: 1961–74). The plates are heated at 94° C. for two minutes, then cooled to 72° C., 1.6 units of T DNA polymerase are added and the cDNA is amplified during thirty heating and cooling cycles. Each cycle consists of the following stages: annealing for one minute at 52° C., elongation for one minute at 52° C. and denaturing for 30 seconds at 93° C. In the final cycle the period of elongation is increased to five minutes. The heat gradients are 0.3° C. s$^{-1}$.

For the spectrophotometric quantification of the products of amplification, 50 microliters of a solution of bisbenzymide are added to the wells at a concentration of 0.1 mg/ml, and the results are read in a spectrofluorometer equipped with a reader of microtitration plates, activating at 353 nm and detecting the wave-length of the maximum fluorescent emission (Cesarone, C. F. et al. (1979), An. al. Biochem. 100: 187–188).

Normal techniques of nucleic acid electrophoresis are used in identifying the products of amplification (Maniatis, T. et al., Molecular Cloning (A Laboratory Manual). Cold Spring Harbor Laboratory (1982)).

Figure 1:
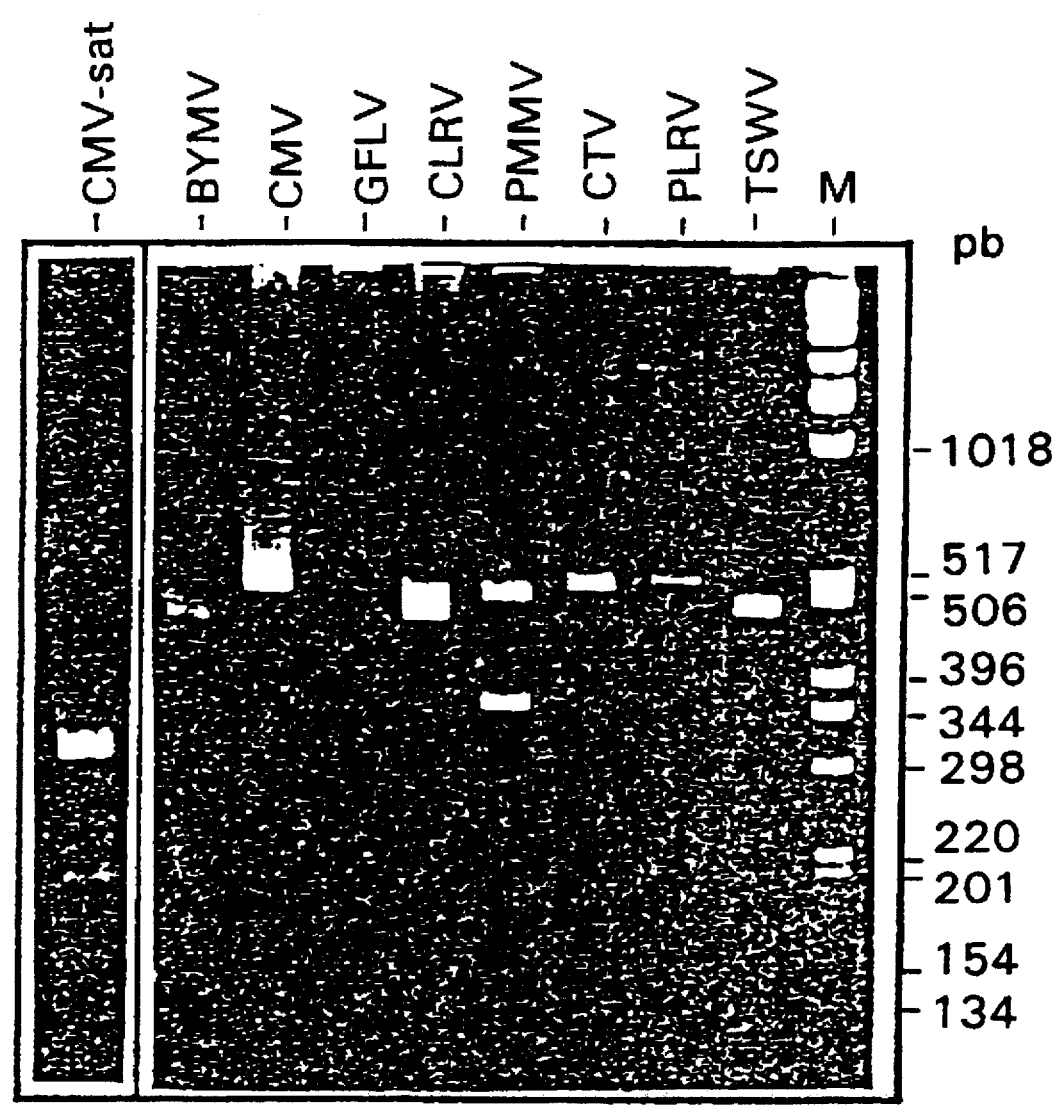

FIG. 1 shows the result obtained. The electrophoretic mobility of the amplified fragment corresponds to that expected for one of 449 pairs of bases.

The spectrophotometric quantification gave the following results:

| BUFFER: | 8 units of fluorescence. |
|---|---|
| HEALTHY BEAN: | 9 units of fluorescence. |
| INFECTED BEAN: | 56 units of fluorescence. |

EXAMPLE 2

Detection and Identification of a Tospovirus

Tospoviruses are viruses that present some of the characteristics of the animal bunyaviruses, such as having a lipid coating, a genome consisting of three molecules of single-stranded RNA, sequential homology and cytoplasmic maturation of their particles (Elliot, R. M. (1990), J. of Gen. Virol. 71: 501–552). A representative member of the group is the tomato spotted-wilt virus (TSWV).

For the detection and identification of in tomato plants (Lycopersicum esculentum L) the procedure described in EXAMPLE 1 was followed. The oligonucleotide primers used (Table 1) were designed on the basis of existing information on the virus genome sequence and flank a fragment of 465 pairs of bases.

FIG. 1 shows the result obtained. The electrophoretic mobility of the fragment amplified corresponds to that expected for one of 465 pairs of bases.

The spectrophotometric quantification gave the following results:

| BUFFER: | 8 units of fluorescence. |
|---|---|
| HEALTHY TOMATO: | 13 units of fluorescence. |
| INFECTED TOMATO: | 380 units of fluorescence. |

TABLE 1

| PATHOGEN | 5' PRIMERS | SEQ ID NO: | 3' PRIMERS | SEQ ID NO: |
|---|---|---|---|---|
| BEAN YELLOW MOSAIC VIRUS | 5'-GCCTTATGGTGTGGTGCATAG-3' | 1 | 5'-CAAGCATGGTGTGCATATCACG-3' | 2 |
| CHERRY LEAF-ROLL VIRUS | 5'-CATGACGAGTGGGCGTC-3' | 3 | 5'-GCGTCGGAAAGATTACG-3' | 4 |
| CUCUMBER MOSAIC VIRUS | 5'-CTAGACATCTGTGACGCGA-3' | 5 | 5'-GCGCGAAACAAGCTTCTTATC-3' | 6 |
| CARNA-5 | 5'-GATGGAGAATTGCGCAGAGGG-3' | 7 | 5'-CATTCACGGAGATCAGCATAGC-3' | 8 |
| CITRUS TRISTEZA VIRUS | 5'-ATGGACGACGAAACAAAGAA-3' | 9 | 5'-CAAGAAATCCGCACACAAGT-3' | 10 |
| GRAPEVINE FANLEAF VIRUS | 5'-CCGTGAGAGGATTGGCTGGTA-3' | 11 | 5'-ATGGGAGGGCAAGTGAGAAAT-3' | 12 |
| POTATO-LEAF-ROLL VIRUS | 5'-CCAGTGGTTRTGGTC-3' | 13 | 5'-GTCTACCTATTTGG-3' | 14 |
| PEPPER MILD MOTTLING VIRUS | 5'-TGTCTGCTATGCTGCCTTCC-3' | 15 | 5'-CCTTTTCCCCTCGTTCTGTAA-3' | 16 |
| POTATO SPINDLE TUBER VIROID | 5'-GGGTTTTCACCCTTCC-3' | 17 | 5'-GAGAAAAAGCGGTTCTCGGG-3' | 18 |
| TOMATO SPOTTED-WILT VIRUS | 5'-ATCAAGCTTCTGAAGGTCAT-3' | 19 | 5'-CTTTGCTTTTCAGCACAGTGCA-3' | 20 |

EXAMPLE 3

Detection and Identification of a Closterovirus

Closteroviruses are viral pathogens. Their particles are elongated, very flexible, with helicoidal symmetry and between 1,250 nm and 2,000 nm in length and their genome is a molecule of single-stranded RNA (Lister, R. M. & Bar-Joseph, M. in Handbook of Plant Virus Infections and Comparative Diagnosis, pp. 809–844. E. Kurstak (Ed.) Elsevier Nort-Holland Biomedical Press (1981)). A representative member of the group is the citrus tristeza virus (CTV).

For the detection and identification of CTV in orange trees (*Citrus sinensis*), the procedure described in EXAMPLE 1 was followed. The oligonucleotide primers used (Table 1) were designed on the basis of existing information on the virus genome sequence (Sekiya, M. E. et al. (1991), J. of Gen. Virol. 72: 1013–1020) and permit the amplification of the first 540 nucleotides of the capsid protein gene.

FIG. 1 shows the results obtained. The electrophoretic mobility of the fragment amplified is as expected for one of 465 pairs of bases.

The spectrophotometric quantification gave the following results:

| BUFFER: | 8 units of fluorescence. |
|---|---|
| HEALTHY ORANGE TREE: | 14 units of fluorescence. |
| INFECTED ORANGE TREE: | 240 units of fluorescence. |

EXAMPLE 4

Detection and Identification of a Tobamovirus

Tobamoviruses are viral pathogens. Their particles are elongated, rigid, of average length (300 nm) and their genome is a linear molecule of single-stranded RNA (Van Regenmortel, M. H. V. (1981) in Handbook of Plant Virus Infections and Comparative Diagnosis. E. Kurstak (Ed.) Elsevier Nort-Holland Biomedical Press (1981). M.Y. Oxford). A representative member of the group is the pepper mild mottling virus (PMMV).

The procedure described in EXAMPLE 1 was followed in order to detect and identify the PMMV in pepper plants (*Capsicum annum*). The oligonucleotide primers used (Table 1) were designed on the basis of existing information on the virus genome sequence (Alonso et al. (1991), J. of Gen. Virol. 72: 2875–2884) and flank a fragment of 496 pairs of bases between nucleotides 735 and 1231.

FIG. 1 shows the results obtained. Two fragments are observed, one with the expected mobility and a second corresponding to a size of 350 pairs of bases owing to the homology (68%) presented by the synthesis primer in direction 5'--3' with the genome fragment between nucleotides 1062 and 1082.

The spectrophotometric quantification gave the following results:

| BUFFER: | 8 units of fluorescence. |
|---|---|
| HEALTHY PEPPER PLANT: | 18 units of fluorescence. |
| INFECTED PEPPER PLANT: | 410 units of fluorescence. |

EXAMPLE 5

Detection and Identification of a Luteovirus

Luteoviruses are viral pathogens. Their particles are icosahedral with an average diameter of 25 nm and their genome is a linear molecule of single-stranded RNA (Rochow, W. F. & Duffus, J. E. (1981). In Handbook of Plant Virus Infections and Comparative Diagnosis. E. Kurstak (Ed.). Elsevier Nort-Holland Biomedical Press, Amsterdam). A representative member of the group is the potato leaf-roll virus (PLRV).

For the detection and identification of PLRV in potato plants (*Solanum tuberosum*) the procedure described in EXAMPLE 1 was followed, increasing the number of amplification cycles to 85 and lowering the temperature during the ringing stage to 41° C. The oligonucleotide primers used (Table 1) were designed on the basis of existing information on the virus sequence (Robertson, N. L. et al. (1991), J. of Gen. Virol. 72: 1473–1477) and flank a fragment of 534 pairs of bases between the nucleotides 3687 and 3701.

FIGS. 1 shows the result obtained. The electrophoretic mobility of the fragment amplified is as expected for one of 534 pairs of bases.

The spectrophotometric quantification gave the following results:

| BUFFER: | 8 units of fluorescence. |
|---|---|
| HEALTHY POTATO PLANT: | 11 units of fluorescence. |
| INFECTED POTATO PLANT: | 72 units of fluorescence. |

EXAMPLE 6

Detection and Identification of a Nepovirus

Nepoviruses are viral pathogens. Their genome are two linear molecules of positive single-stranded RNA individually encapsulated in icosahedral particles with an average diameter of 28 nm (Murant, A. F. In Handbook of Plant Virus Infections and Comparative Diagnosis. 198 pp. E. Kurstak (Ed.). Elsevier Nort-Holland. Biomedical Press, Amsterdam). Two representative members of the group are the cherry leaf-roll virus (CLRV) and the grapevine fanleaf virus (GFLV).

To detect and identify CLRV in the walnut (*Juglans regia*) and GFLV in the grapevine (*Vitis vinifera*) the procedure described in EXAMPLE 1 was followed. The oligonucleotide primers used were designed on the basis of existing information on sequences of CLRV (Borja, M. J. & Ponz, F. (1992), J. of Virol. Meth. 36: 73–83) and GFLV (Sánchez, F. et al. (1991), Nucleic Acid Res. 19: 5440). In the case of GFLV, a fragment corresponding to the first 568 nucleotides of the cistron of the capsid protein was amplified, and in that of CLRV one of 448 pairs of bases between the nucleotides 1194 and 1642 of the 3'-UTR.

FIG. 1 shows the results obtained. The electrophoretic mobility corresponds to that expected for fragments of 568 and 448 pairs of bases.

The spectrophotometric quantification gave the following results:

| BUFFER: | 8 units of fluorescence. |
|---|---|
| HEALTHY WALNUT TREE: | 14 units of fluorescence. |
| INFECTED WALNUT TREE: | 560 units of fluorescence. |
| HEALTHY VINE: | 11 units of fluorescence. |
| INFECTED VINE: | 65 units of fluorescence. |

EXAMPLE 7

Detection and Identification of a Cucumovirus

Cucumoviruses are viral pathogens. Their particles are isometric, approximately 30 nm in diameter, and their genome are three molecules of positive single-stranded RNA (Kaper, J. M. & Waterworth (1981), in Handbook of Plant Virus Infections and Comparative Diagnosis. 257 pp. E. Kurstak (Ed.). Elsevier Nort-Holland. Biomedical Press, Amsterdam). A representative member of the group is the cucumber mosaic virus (CMV).

The procedure described in EXAMPLE 1 was followed in the detection and identification of CMV in tobacco plants (*Nicotiana tabacum*). The oligonucleotide primers used (Table 1) were designed on the basis of existing information on the virus genome sequence (Quemada, H. et al. (1989), J. Gen. Virol. 70: 1065–1073) and flank a fragment of 541 pairs of bases between nucleotides 112 and 653 of the RNA3.

FIG. 1 shows the result obtained. The electrophoretic mobility of the fragment amplified is as expected for one of 541 pairs of bases.

The spectrophotometric quantification gave the following results:

| BUFFER: | 8 units of fluorescence. |
|---|---|
| HEALTHY TOBACCO: | 14 units of fluorescence. |
| INFECTED TOBACCO: | 620 units of fluorescence. |

EXAMPLE 8

Detection and Identification of a Satellite RNA

Satellite RNAs are subviral pathogens exclusive to plants. Their genome is a linear molecule of positive single-stranded RNA which does not codify for any structural protein. They use the capsid protein of a plant virus to form their particles (Matthews, R. E. F. (1991), Viroids, Satellite Viruses and Satellite RNAs. In Plant Virology, 306 pp. Academic Press, New York).

In this example we describe the detection and identification of CARNA-5, a satellite RNA of the cucumber mosaic virus (CMV) in pepper plants (*Capsicum anuum*). The procedure followed is that described in EXAMPLE 1 except that an antibody against double-chain RNAs was used in lining the wells of the microtitration plate. The oligonucleotide primers used (Table 1) were designed on the basis of information regarding the satellite RNA sequence (Kaper, J. M. et al. 1988), Virology, 163: 284–292) and flank a fragment of 303 pairs of bases between nucleotides 10 and 312.

FIG. 1 shows the result obtained. The electrophoretic mobility of the amplified fragment corresponds to that expected for one of 303 pairs of bases.

The spectrophotometric quantification gave the following results:

| BUFFER: | 8 units of fluorescence. |
|---|---|
| HEALTHY PEPPER PLANT: | 16 units of fluorescence. |
| INFECTED PEPPER PLANT: | 420 units of fluorescence. |

EXAMPLE 9

Detection and Identification of a Viroid

Viroids are subviral pathogens exclusive to plants. Their genome is a circular molecule of single-stranded RNA that does not codify for any structural protein (Matthews, R. E. F.).

In this example we describe the detection and identification of the potato spindle tuber viroid (PSTVd). The procedure followed is that described in EXAMPLE 1, except that an antibody against double-stranded RNAs was used in lining the cups of the microtitration plate. The oligonucleotide primers used (Table 1) were designed on the basis of information on the viroid genome sequence (Gross et al. (1978), Nature (London) 273: 203–208) and flank a fragment of 258 pairs of bases between nucleotides (349-1).

Figure 3:
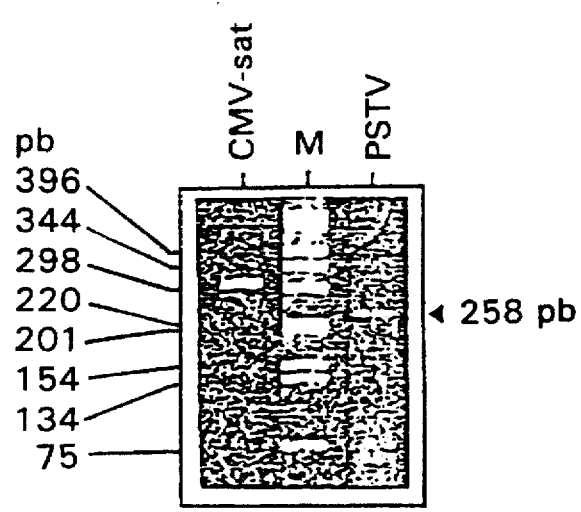
FIG. 3 shows the results obtained, in terms of electrophoretic mobility, of the procedures performed for identification and detection of pathogens according to Example 9.

The result obtained is shown in FIG. 3. The electrophoretic mobility of the amplified fragment corresponds to that expected for one of 258 pairs of bases.

The spectrophotometric quantification gave the following results:

| BUFFER: | 8 units of fluorescence. |
|---|---|
| HEALTHY POTATO: | 15 units of fluorescence. |
| INFECTED POTATO: | 380 units of fluorescence. |

EXAMPLE 10

Detection and Identification of Viral Pathogens using Antibodies against Double-Chain RNAs FIG. 2 shows the results obtained when using antibodies against double-stranded RNAs in the detection and identification of the following viral pathogens:

a) Bean yellow mosaic virus in broad-bean plants.

b) Cucumber mosaic virus in tobacco plants.

c) Grapevine fanleaf virus in grapevines.

d) Cherry leaf-roll virus in walnut trees.

The procedure followed is that described in the preceding examples.

---

We claim:

1. A method for detecting at least one specific viral or subviral pathogen in a sample without stages of intermediate denaturing of the viral or subviral pathogen consisting essentially of the following steps:
   a) Providing a substrate on which antibodies are immobilized, said antibodies having specificity against a component of a viral or subviral pathogen;
   b) Permitting the contact of a test sample with said immobilized antibodies of step a) to thereby immobilize said viral or subviral pathogen present;
   c) Providing at least one DNA primer complementary to an enzymatically amplifiable fragment or the total genome of said viral or subviral pathogen, said primer being of a length sufficient to hybridize stably and specifically to said fragment or said total genome;
   d) Permitting the hybridization of said DNA primer to said immobilized fragment or total genome of said viral or subviral pathogen;
   e) Synthesizing complementary DNA (cDNA) to said fragment or total genome of said viral or subviral pathogen using said primer;
   f) Enzymatically amplifying said DNA, forming amplification products; and
   g) Detecting said amplification products using spectrophotometric means which measure double-stranded DNA.

2. The method according to claim 1, wherein the amplification products are quantified.

3. The method according to claim 2, wherein the substrate is compartmentalized.

4. The method of claim 2, wherein said component of a viral or subviral pathogen comprises the group consisting of a viral structural protein, double-stranded DNA, double-stranded RNA or single-stranded RNA.

5. The method of claim 2, wherein said substrate is a microtiter plate.

6. The method of claim 2, wherein the viral pathogen is an animal virus.

7. The method of claim 2, wherein the viral pathogen is a plant virus.

8. The method of claim 2, wherein the viral pathogen is a fungal virus.

9. The method of claim 2, wherein the viral pathogen is a bacterial virus.

10. The method of claim 2, wherein said pathogen is a viral pathogen of viruses.

11. The method of claim 2, wherein said pathogen is a subviral pathogen.

12. The method of claim 2, wherein said pathogen is a viroid.

13. The method of claim 2, wherein said pathogen is a viral satellite.

14. The method of claim 2, wherein said pathogen is viral satellite RNA.

15. The method of claim 2, wherein said pathogen is a virusoid.

16. A method for detecting, quantifying, and identifying at least one viral or subviral pathogen in a test sample without stages of intermediate denaturing of the viral or subviral pathogen consisting essentially of the following steps:
   a) Providing a substrate on which antibodies are immobilized, said antibodies having specificity against a component of a viral or subviral pathogen;
   b) Permitting the contact of a test sample with said immobilized antibodies of step a) to thereby immobilize said viral or subviral pathogen present;
   c) Providing at least one DNA primer complementary to an enzymatically amplifiable fragment or the total genome of said viral or subviral pathogen, said primer and fragment being of a length to hybridize stably and specifically to said fragment or total genome;
   d) Permitting the hybridization of said complementary DNA primer to said immobilized fragment or total genome of said viral or subviral pathogen;
   e) Synthesizing a fragment or total genome of said viral or subviral pathogen using said primer;
   f) Enzymatically amplifying said cDNA or said cDNA and said fragment of the genome when said pathogen is a DNA virus, forming amplification products;
   g) Detecting and quantifying said amplification products using spectrophotometric means which measure double-stranded DNA; and
   h) Confirming the identity of said amplification products using electrophoretic means.

17. The method according to claim 16, wherein the substrate is compartmentalized.

18. The method of claim 16, wherein said substrate is a microtiter plate.

19. The method of claim 16, wherein the viral pathogen is an animal virus.

20. The method of claim 16, wherein the viral pathogen is a plant virus.

21. The method of claim 16, wherein the viral pathogen is a fungal virus.

22. The method of claim 16, wherein the viral pathogen is a bacterial virus.

23. The method of claim 16, wherein said pathogen is a viral pathogen of viruses.

24. The method of claim 16, wherein said pathogen is a subviral pathogen.

25. The method of claim 16, wherein said pathogen is a viroid.

26. The method of claim 16, wherein said pathogen is a viral satellite.

27. The method of claim 16, wherein said pathogen is viral satellite RNA.

28. The method of claim 16, wherein said pathogen is a virusoid.

29. A method according to claim 1 wherein the spectrophotometric means comprises adding a solution of bisbenzymide after step f).

30. A method according to claim 16 wherein the spectrophotometric means comprises adding a soution of bisbenzymide after step f).

31. A kit for the detection and identification of at least one viral or subviral pathogen in a test sample comprising
   a) a substrate on which antibodies are immobilized, said antibodies having specificity against a component of said viral or subviral pathogen and
   b) DNA amplification primers wherein at least one DNA primer is complementary to an enzymatically amplifiable fragment or the total genome of said viral or subviral pathogen wherein said viral or subviral pathogen is selected from the group consisting of bean yellow mosaic virus, cherry leaf-roll virus, cucumber mosaic virus, CARNA-5, citrus tristeza virus, grapevine fanleaf virus, potato leaf-roll virus, pepper mild mottling virus, potato spindle tuber viroid, tomato spotted-wilt virus and said DNA amplifications primer are selected from the group consisting of the primers listed in FIG. 4 and primers having sufficient complementary primers listed in FIG. 4 to bind stably and specifically to said fragment or total genone of said viral or subviral pathogen.

32. A method for the detection and identification of at least one viral or subviral pathogen in a test sample without stages of intermediate denaturing of the viral or subviral pathogen consisting essentially of the following steps:
   a) Providing a substrate on which antibodies are immobilized, said antibodies having specificity against a component of said viral or subviral pathogen, wherein said viral or subviral pathogen is selected from the group comprising bean yellow mosaic virus, cherry leaf-roll virus, cucumber mosaic virus, CARNA-5, citrus tristeza virus, grapevine fanleaf virus, potato leaf-roll virus, pepper mild mottling virus, potato spindle tuber viroid, and tomato spotted-wilt virus;
   b) Permitting the contact of said test sample with said immobilized antibodies of step a) to thereby immobilize said viral or subviral pathogen present;
   c) Providing at least one DNA primer complementary to an enzymatically amplifiable fragment or the total genome of said viral or subviral pathogen, wherein the DNA primer is selected from the group consisting of the primers listed in FIG. 4 and primers having sufficient complementarity to said primers listed in FIG. 4 to bind stably and specifically to said fragment or total genome of said viral or subviral pathogen;
   d) Permitting the hybridization of said DNA primer to said immobilized viral or subviral pathogen;
   e) Synthesizing complementary DNA (cDNA) to said fragment or total genome of said viral or subviral pathogen using said primer;
   f) Enzymatically amplifying said cDNA or said cDNA and said fragment of the genome when said pathogen is a DNA virus, forming amplification products; and
   g) Detecting, quantifying, and/or identifying said amplification products using spectrophotometric or electrophoretic means.

33. The method according to claim 32, wherein the substrate is compartmentalized.

34. A method for detecting at least one specific viral or subviral pathogen in a sample comprising the following steps:
   a) providing a substrate on which antibodies are immobilized, said antibodies having specificity against a component of a viral or subviral pathogen;
   b) permitting the contact of a test sample with said immobilized antibodies of step a) to thereby immobilize said viral or subviral pathogen present;
   c) providing, without releasing nucleic acid of the viral or subviral pathogen, at least one DNA primer complementary to an enzymatically amplifiable fragment or the total genome of said viral or subviral pathogen, said primer being of a length sufficient to hybridize stably and specifically to said fragment or said total genome;
   d) permitting the hybridization of said DNA primer to said immobilized fragment or total genome of said viral or subviral pathogen;
   e) synthesizing complementary DNA (cDNA) to said fragment or total genome of said viral or subviral pathogen using said primer;
   f) enzymatically amplifying said DNA, forming amplification products; and
   g) detecting said amplification products using spectrophotometric means which measure double-stranded DNA.

35. A method for detecting, quantifying, and identifying at least one viral or subviral pathogen in a test sample comprising the following steps:
   a) providing a substrate on which antibodies are immobilized, said antibodies having specificity against a component of a viral or subviral pathogen;
   b) permitting the contact of a test sample with said immobilized antibodies of step a) to thereby immobilize said viral or subviral pathogen present;
   c) providing, without releasing nucleic acid of the viral or subviral pathogen, at least one DNA primer complementary to an enzymatically amplifiable fragment or the total genome of said viral or subviral pathogen, said primer and fragment being of a length to hybridize stably and specifically to said fragment or total genome;
   d) permitting the hybridization of said complementary DNA primer to said immobilized fragment or total genome of said viral or subviral pathogen;
   e) synthesizing a fragment or total genome of said viral or subviral pathogen using said primer;
   f) enzymatically amplifying said cDNA or said cDNA and said fragment of the genome when said pathogen is a DNA virus, forming amplification products; and
   g) detecting and quantifying said amplification products using spectrophotometric means which measure double-stranded DNA; and
   h) confirming the identity of said amplification products using electrophoretic means.

36. A method for the detection and identification of at least one viral or subviral pathogen in a test sample comprising the following steps:
   a) providing a substrate on which antibodies are immobilized, said antibodies having specificity against a component of said viral or subviral pathogen, wherein said viral or subviral pathogen is selected from the group consisting of bean yellow mosaic virus, cherry leaf-roll virus, cucumber mosaic virus, CARNA-5, citrus tristeza virus, grapevine fanleaf virus, potato leaf-roll virus, pepper mild mottling virus, potato spindle tuber viroid, and tomato spotted-wilt virus;
   b) permitting the contact of said test sample with said immobilized antibodies of step a) to thereby immobilize said viral or subviral pathogen present;

c) providing, without releasing nucleic acid of the viral or subviral pathogen, at least one DNA primer complementary to an enzymatically amplifiable fragment or the total genome of said viral or subviral pathogen, wherein the DNA primer is selected from the group consisting of the primers listed in FIG. 4 and primers having sufficient complementarity to said primers listed in FIG. 4 to bind stably and specifically to said fragment or total genome of said viral or subviral pathogen;

d) permitting the hybridization of said DNA primer to said immobilized viral or subviral pathogen;

e) synthesizing complementary DNA (cDNA) to said fragment or total genome of said viral or subviral pathogen using said primer;

f) enzymatically amplifying said cDNA or said cDNA and said fragment of the genome when said pathogen is a DNA virus, forming amplification products; and g) detecting, quantifying, and/or identifying said amplification products using spectrophotometric or electrophoretic means.

* * * * *

UNITED STATES PATENT AND TRADEMARK OFFICE
CERTIFICATE OF CORRECTION

PATENT NO. :   5,714,312
DATED      :   Feb. 3, 1998
INVENTOR(S):   Nuno Barbosa Nolasco et al.

It is certified that error appears in the above-identified patent and that said Letters Patent is hereby corrected as shown below:

On the title page,
Item No. [75] Inventors, in the first-named inventor's name, change "Bardosa" to --Barbosa--.

Item No. [75], change "Pons" to --Ponz--; change "Vincente" to --Vicente--.

Under Item No. [73] Assignee, change "Techologia" to --Tecnologia--.

Signed and Sealed this

Tenth Day of November 1998

Attest:

BRUCE LEHMAN

*Attesting Officer*     *Commissioner of Patents and Trademarks*

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:

( A ) LENGTH: 21 base pairs ( B ) TYPE: nucleic acid ( C ) STRANDEDNESS: single ( D ) TOPOLOGY: linear ( x i ) SEQUENCE DESCRIPTION: SEQ ID NO:1:

GCCTTATGGT GTGGTGCATA G                                                                                21

( 2 ) INFORMATION FOR SEQ ID NO:2:

( i ) SEQUENCE CHARACTERISTICS:
       ( A ) LENGTH: 22 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:2:

CAAGCATGGT GTGCATATCA CG                                                                               22

( 2 ) INFORMATION FOR SEQ ID NO:3:

( i ) SEQUENCE CHARACTERISTICS:
       ( A ) LENGTH: 17 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:3:

CATGACGAGT GGGCGTC                                                                                     17

( 2 ) INFORMATION FOR SEQ ID NO:4:

( i ) SEQUENCE CHARACTERISTICS:
       ( A ) LENGTH: 17 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:4:

GCGTCGGAAA GATTACG                                                                                     17

( 2 ) INFORMATION FOR SEQ ID NO:5:

( i ) SEQUENCE CHARACTERISTICS:
       ( A ) LENGTH: 19 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:5:

CTAGACATCT GTGACGCGA                                                                                   19

( 2 ) INFORMATION FOR SEQ ID NO:6:

( i ) SEQUENCE CHARACTERISTICS:
       ( A ) LENGTH: 21 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:6:

GCGCGAAACA AGCTTCTTAT C                                                                                21

( 2 ) INFORMATION FOR SEQ ID NO:7:

( i ) SEQUENCE CHARACTERISTICS:
       ( A ) LENGTH: 21 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:7:

GATGGAGAAT TGCGCAGAGG G                                                                                21

( 2 ) INFORMATION FOR SEQ ID NO:8:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

CATTCACGGA GATCAGCATA GC                                  22

( 2 ) INFORMATION FOR SEQ ID NO:9:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

ATGGACGACG AAACAAAGAA                                    20

( 2 ) INFORMATION FOR SEQ ID NO:10:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

CAAGAAATCC GCACACAAGT                                    20

( 2 ) INFORMATION FOR SEQ ID NO:11:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

CCGTGAGAGG ATTGGCTGGT A                                  21

( 2 ) INFORMATION FOR SEQ ID NO:12:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

ATGGGAGGGC AAGTGAGAAA T                                  21

( 2 ) INFORMATION FOR SEQ ID NO:13:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

CCAGTGGTTR TGGTC                                              15

( 2 ) INFORMATION FOR SEQ ID NO:14:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

GTCTACCTAT TTGG 14

( 2 ) INFORMATION FOR SEQ ID NO:15:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:15:

TGTCTGCTAT GCTGCCTTCC 20

( 2 ) INFORMATION FOR SEQ ID NO:16:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:16:

CCTTTTCCCC TCGTTCTGTA A 21

( 2 ) INFORMATION FOR SEQ ID NO:17:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:17:

GGGTTTTCAC CCTTCC 16

( 2 ) INFORMATION FOR SEQ ID NO:18:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:18:

GAGAAAAAGC GGTTCTCGGG 20

( 2 ) INFORMATION FOR SEQ ID NO:19:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:19:

ATCAAGCTTC TGAAGGTCAT 20

( 2 ) INFORMATION FOR SEQ ID NO:20:

```
( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:20:

CTTTGCTTTT CAGCACAGTG CA                                    22
```